(12) United States Patent
Schmidt et al.

(10) Patent No.: US 10,052,429 B2
(45) Date of Patent: Aug. 21, 2018

(54) DEVICES AND METHODS FOR LUNG VOLUME REDUCTION

(71) Applicant: Boston Scientific Scimed, Inc., Maple Grove, MN (US)

(72) Inventors: Brian L. Schmidt, White Bear Lake, MN (US); Bryan Allen Clark, Forest Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 544 days.

(21) Appl. No.: 14/724,467

(22) Filed: May 28, 2015

(65) Prior Publication Data

US 2015/0343169 A1 Dec. 3, 2015

Related U.S. Application Data

(60) Provisional application No. 62/004,511, filed on May 29, 2014.

(51) Int. Cl.
*A61M 25/00* (2006.01)
*A61M 1/36* (2006.01)
*A61K 9/00* (2006.01)
*A61M 16/00* (2006.01)

(52) U.S. Cl.
CPC ......... *A61M 1/3659* (2014.02); *A61K 9/0024* (2013.01); *A61M 16/00* (2013.01)

(58) Field of Classification Search
CPC .... A61K 9/0024; A61M 1/3659; A61M 16/00
See application file for complete search history.

(56) References Cited

U.S. PATENT DOCUMENTS

| | | | |
|---|---|---|---|
| 6,200,336 B1* | 3/2001 | Pavcnik | A61F 2/07 623/1.13 |
| 7,913,698 B2 | 3/2011 | Barry et al. | |
| 9,883,911 B2* | 2/2018 | Farritor | A61B 34/30 |
| 2003/0050635 A1* | 3/2003 | Truckai | A61B 18/1492 606/41 |
| 2007/0027554 A1* | 2/2007 | Biran | A61L 31/146 623/23.74 |
| 2011/0152902 A1* | 6/2011 | Kurrus | A61B 17/12022 606/158 |
| 2013/0184658 A1* | 7/2013 | Duncan | A61B 17/1214 604/264 |

OTHER PUBLICATIONS

Shah et al., "Design of the exhale airway stents for emphysema (EASE) trial: an endoscopic procedure for reducing hyperinflation", Jan. 7, 2011, vol. 11, No. 1, BMC Pulmonary Medicine (8 pages).

(Continued)

*Primary Examiner* — Matthew F Desanto
(74) *Attorney, Agent, or Firm* — Bookoff McAndrews, PLLC

(57) ABSTRACT

Methods and devices for treating a lung are disclosed. The method may include deploying a catheter into a blood vessel directing blood towards a portion of the lung, and discharging a media into the blood vessel through the catheter, the media may be configured to at least partially block the flow of blood within the portion of the lung.

8 Claims, 5 Drawing Sheets

(56) References Cited

OTHER PUBLICATIONS

Herth et al., "Characterization of outcomes 1 year after endoscopic thermal vapor ablation for patients with heterogeneous emphysema", International Journal of COPD, 2012, pp. 397-405, vol. 7, Dove Medical Press Ltd. (9 pages).
Worcestor, Sharon, "Lung-Volume Reduction Coils Boost Walk Distance", Nov. 1, 2012, American College of Surgeons: ACS Surgery News, International Medical News Group, LLC (2 pages).
Zaid et al., "6 and 12 month outcomes following RePneu bronchoscopic lung vol. reduction coil treatment", 2013, European Respiratory Society: Annual Congress 2013 (1 page).
Falkenstern-Ge et al., "Treatment of Severe Advanced Emphysema With Lung Volume Reduction Using Lung Sealant: A Case Report of 2 Patients", Jan. 2013, pp. 58-62, vol. 20, No. 1, Journal of Bronchology & Interventional Pulmonology (5 pages).
Venuta et al., "One-Way Valves for Bronchoscopic Lung Volume Reduction", Jun. 15, 2008, The Cardiothoracic Surgery Network, accessed Mar. 28, 2015, <http://www.ctsnet.org/print/portals/thoracic/newtechnology/article-3> (5 pages).
Springmeyer et al., "Development of a Bronchial Valve for Treatment of Severe Emphysema", Apr. 8, 2008, The Cardiothoracic Surgery Network, accessed Mar. 28, 2015, <http://www.ctsnet.org/print/portals/thoracic/newtechnology/article-10> (7 pages).
Galluccio et al., "Bronchoscopic lung volume reduction for pulmonary emphysema: preliminary experience with a new NOVATECH® endobronchial silicone one-way valve", 2010, pp. 213-215, Interactive Cardiovascular and Thoracic Surgery, European Association for Cardio-Thoracic Surgery (3 pages).
Watanabe et al., "Bronchial Occlusion With Endobronchial Watanabe Spigot", Oct. 2003, pp. 264-267, vol. 10, No. 4, Journal of Bronchology & Interventional Pulmonology (4 pages).

\* cited by examiner

DEVICES AND METHODS FOR LUNG VOLUME REDUCTION

CROSS-REFERENCE TO RELATED APPLICATION

This patent application claims the benefit of priority to U.S. Provisional Application No. 62/004,511, filed on May 29, 2014, the entirety of which is incorporated herein by reference.

TECHNICAL FIELD

The disclosed embodiments relate to devices and methods for lung volume reduction to improve lung function. More particularly, the present disclosure relates to devices and methods of lung volume reduction via the pulmonary circulation.

BACKGROUND

Chronic Obstructive Pulmonary Disease (COPD) comprises chronic bronchitis and emphysema. COPD is a serious progressive lung disease which makes it harder to breath. COPD currently affects over fifteen million people in the United States alone and is currently a leading cause of death worldwide. The economic and social burden of the disease is both substantial and increasing.

Chronic bronchitis is characterized by chronic cough with sputum production. The resulting airway inflammation causes eventual fibrosis of the lung airway walls, causing significant reduction in gas exchange capability of the lungs. Emphysema is characterized by the destruction of the lung parenchyma, the functioning part of the lungs. This destruction of the lung parenchyma leads to a loss of elastic recoil and tethering which maintains airway patency. Because bronchioles of the lung are not supported by cartilage like the larger airways are, they have little intrinsic support and therefore are susceptible to collapse when destruction of tethering occurs, particularly during exhalation. The loss in elastic recoil in COPD patients leads to air trapping and hyperinflation of the lungs. The result is poor respiration (gas exchange) and increased residual volume of the lungs leading to increased CO2 retention and reduced O2 supply to the alveoli of the lungs.

One existing approach to treat COPD is lung volume reduction surgery (LVRS), where a portion of diseased lung is removed surgically, for improved functioning of the remaining lung tissue. By removing the diseased portion of a lung, the remaining healthier alveoli are able to inflate more fully and lung function is improved. However, LVRS carries with it substantial risk due to its invasive nature. Another approach is to block diseased portions of the lung by blocking airways leading to these portions. However, presence of collateral airflow pathways in the lungs may decrease the effectiveness of this approach. The devices and methods of the current disclosure may enable lung volume reduction without one or more of the limitations discussed above.

SUMMARY

The disclosed embodiments relate to devices and methods for non-surgically reducing lung volume for treating, for example, chronic obstruction pulmonary diseases. In one aspect, a method of treating a lung is disclosed. The method may include deploying a catheter into a blood vessel directing blood towards a targeted portion of the lung, and discharging a media into the blood vessel through the catheter. The media may be configured to at least partially block the flow of blood within the targeted portion or portions of the lung.

Additionally or alternatively, in some aspects, deploying the catheter into a blood vessel may include deploying the catheter into the pulmonary artery; the media may be one of a solid or a gel that solidifies in the blood vessel; the media may be a temporary media that permits restoration of the flow of blood within the targeted portion of the lung after a first time, and the method may include discharging a second media into the blood vessel to block the flow of blood within the targeted portion after the restoration, wherein the second media may be different from the temporary media; deploying the catheter may include deploying the catheter into the blood vessel through one of the superior vena cava or the inferior vena cava; wherein after discharge in the blood vessel, the media is configured to dissipate in the presence of a chemical or when exposed to radiant energy; deploying the catheter includes deploying the catheter into a blood vessel that directs blood from a heart to the lung; discharging a media may include discharging a media that expands after being discharged in the blood vessel; discharging a media may include discharging a plurality of media that interlock to at least partially block the flow of blood within the targeted portion; and the media may be drug-eluting.

In another aspect, a method of treating a lung is disclosed. The method may include deploying a catheter into a blood vessel that directs blood from a heart to a lung, and discharging a media into the blood vessel at a discharge site. The media may be configured to flow with blood in the blood vessel and block the flow of blood within a targeted portion of the lung.

Additionally or alternatively, in some aspects, the media may be a metal or a polymer; the media may expand in the blood vessel after the discharging; deploying a catheter may include deploying the catheter into the pulmonary artery; deploying the catheter may include deploying the catheter into the bronchial artery; the media may be a temporary media that permits restoration of the flow of blood within the targeted portion of the lung after a first time, and the method may further include discharging a second media into the blood vessel to block the flow of blood within the targeted portion after the restoration, wherein the second media may be different from the temporary media; the temporary media may dissolve to restore the flow of blood.

In a further aspect, a device for treating an airway of a lung is disclosed. The device may include a catheter configured for insertion into a blood vessel that directs blood from a heart to the lung, and a media configured for discharge in the blood vessel, wherein the media is configured to at least partially block a flow of blood to a targeted portion within the lung.

Additionally or alternatively, in some aspects, the media is configured to expand in the blood vessel after discharge; the media is a solid or a gel that is configured to solidify after discharge; and the media is a metal or a polymer.

BRIEF DESCRIPTION OF THE DRAWINGS

The drawings illustrate the design and utility of exemplary embodiments of the present disclosure, in which similar elements are referred to by common reference numerals. In order to better appreciate how the above-disclosed and other advantages and objects of the present disclosure are obtained, a more detailed description of the present embodiments will be rendered by reference to the accompanying drawings. Understanding that these drawings depict only exemplary embodiments of the disclosure and are not therefore to be considered limiting in scope, the disclosure will be described and explained with additional specificity and detail through the use of the accompanying drawings in which.

DETAILED DESCRIPTION OF EXEMPLARY EMBODIMENTS

The present disclosure is drawn to devices and methods for the treatment of diseased tissue. Such diseased tissue may suffer from COPD and/or other lung conditions, such as asthma. Exemplary embodiments are drawn to devices and methods for the treatment of diseased tissue in the lungs. In some embodiments, the treatment may include inducing necrosis or atelectasis of one or more diseased portions of the lungs to substantially reduce or prevent inhaled air from reaching diseased portions. As inhaled air is no longer directed to diseased portions of the lungs, the remaining healthy tissues receive more air, and lung function improves. While the principles of the present disclosure are described with reference to treatments for the lungs of a patient, it should be understood that the disclosure is not limited thereto. Rather, the devices and methods may find applicability for the treatment of any luminal tissue structure.

Figure 1:
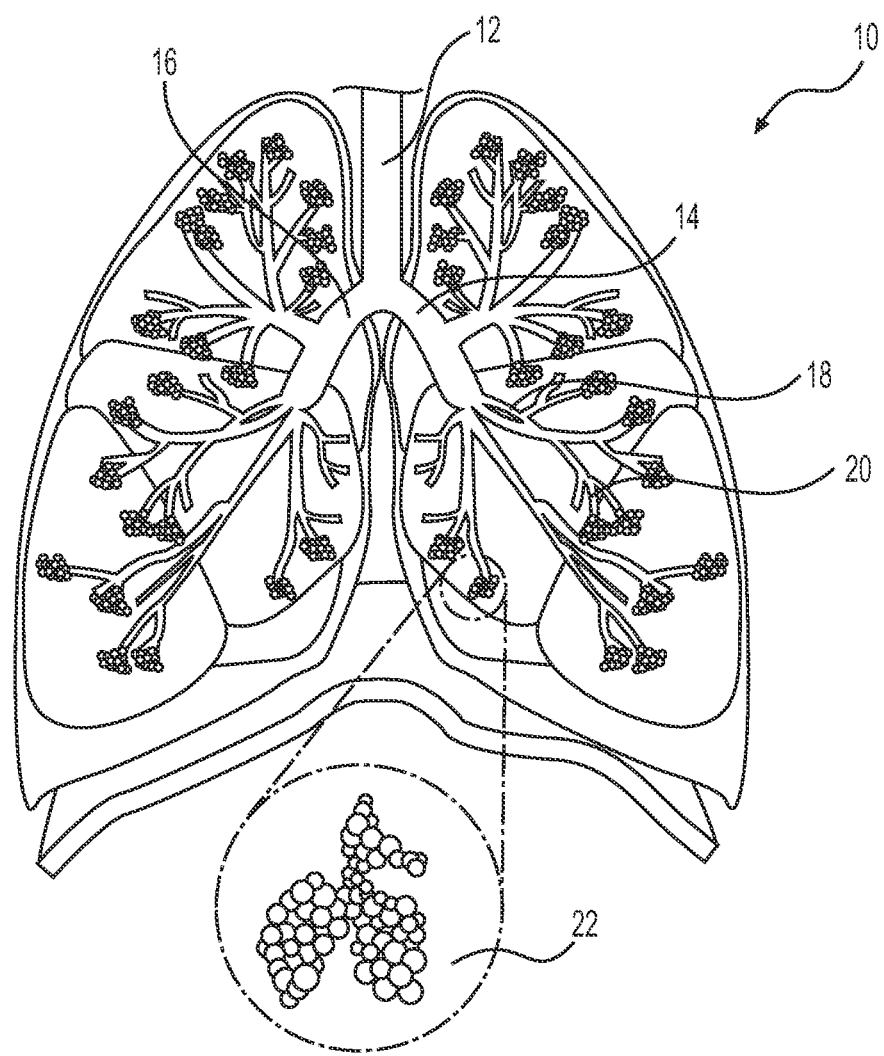
FIG. 1 illustrates the anatomy of the lungs of an individual.

FIG. 1 depicts a pair of lungs 10 in an individual. A wind pipe or trachea 12 connects the nose (not shown) and mouth (not shown) to the lungs 10. As the individual inhales, the diaphragm and intercostal muscles between the ribs contract and expand the chest cavity. This expansion lowers the pressure in the chest cavity below the outside air pressure and causes the air to flow in through the airways and inflate the lungs. When the individual exhales, the diaphragm and intercostal muscles relax and the chest cavity gets smaller. The decrease in volume of the cavity increases the pressure in the chest cavity above the outside air pressure causing the air from the lungs to flow out of the lungs. The cycle then repeats with each breath. As air flows in through the nose and mouth, the trachea 12 transports the air to the lungs 10 for respiratory functions. The trachea 12 divides into the left 14 and right 16 bronchus stems, which further divide into a plurality of bronchi 18, bronchioles 20, and eventually, terminate in a plurality of alveoli 22. The alveoli 22 are small air sacs which enable gas exchange with the individual's blood stream. That is, they permit oxygen diffusion into the blood stream, and receive and expel $CO_2$ during exhalation.

Figure 2:
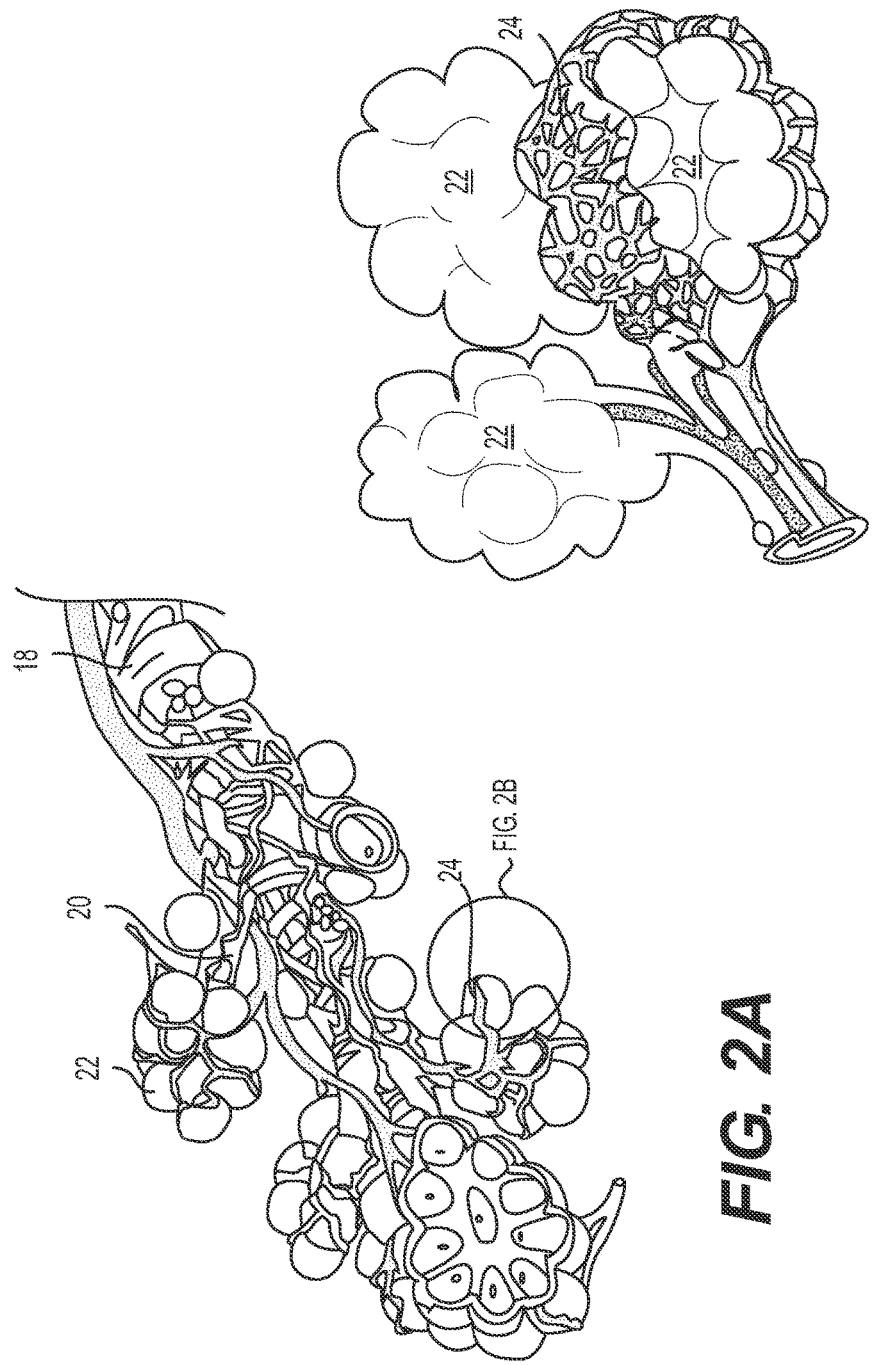
FIG. 2A illustrates blood vessels in a portion of the lungs of FIG. 1.
FIG. 2B illustrate the blood vessels in an alveoli of the lungs of FIG. 1.

FIGS. 2A and 2B illustrate blood vessels in the lungs that permit gas exchange between the lungs and the blood. The alveoli 22 are wrapped in a fine mesh of capillaries 24 that transport blood between the lungs and the heart. The capillaries 24 form a close contact with the alveolar-capillary membranes of the alveoli 22, and allow gas diffusion to take place between the membranes and the capillaries 24. Diffusion is the process by which molecules of higher concentration pass across the membrane to a lower concentration area. The oxygen concentration in the alveoli 22 will be higher than deoxygenated blood in the capillaries 24, therefore oxygen from the alveoli 22 diffuses through the membrane and enters the blood within the capillaries 24. Similarly, due to higher concentration of carbon dioxide ($CO_2$) in the capillaries 24, $CO_2$ from the blood diffuses through the membrane and enters the alveoli 22. This $CO_2$ is exhaled out of the alveoli 22 during the breathing process. The oxygenated blood in the capillaries 24 flows to the heart from where it is pumped to the rest of the body.

Figure 3:
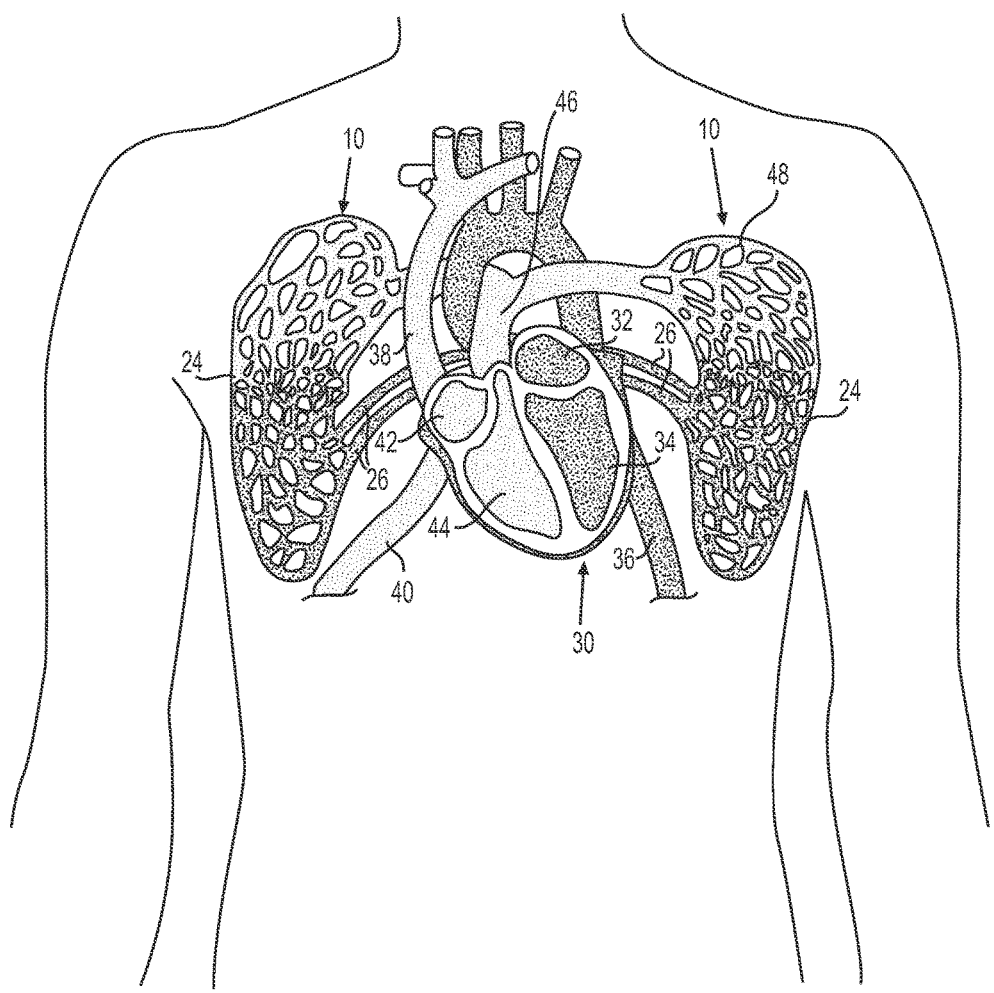
FIG. 3 illustrates the network of blood vessels that connect the heart and the lungs of FIG. 1.

FIG. 3 illustrates the network of blood vessels that connect the heart 30 and the lungs 10. The oxygenated blood from the capillaries 24 of the lungs 10 flow into four pulmonary veins 26 that open into the left atrium 32 of the heart 30. When the left atrium contracts as the heart beats, blood travels through the mitral valve (not shown) into the left ventricle 34. The left ventricle 34 pumps the oxygenated blood to the rest of the body through the aorta 36. After depleting the oxygen, the deoxygenated blood from the body flows back to the heart 30 through the superior and inferior vena cava 38, 40. The superior vena cava 38 collects blood from the upper half of the body and the inferior vena cava 40 collects blood from the lower half of the body. This deoxygenated blood enters the right atrium 42 of the heart 30. When the right atrium 42 contracts, the blood goes through the tricuspid valve (not shown) into the right ventricle 44. When the right ventricle 44 contracts, the deoxygenated blood is pumped through the pulmonary artery 46 to the lungs 10. The pulmonary artery 46 forms smaller blood vessels called arterioles 48 which direct the blood flow to the capillaries 24 surrounding lung alveoli 22.

Figure 4:
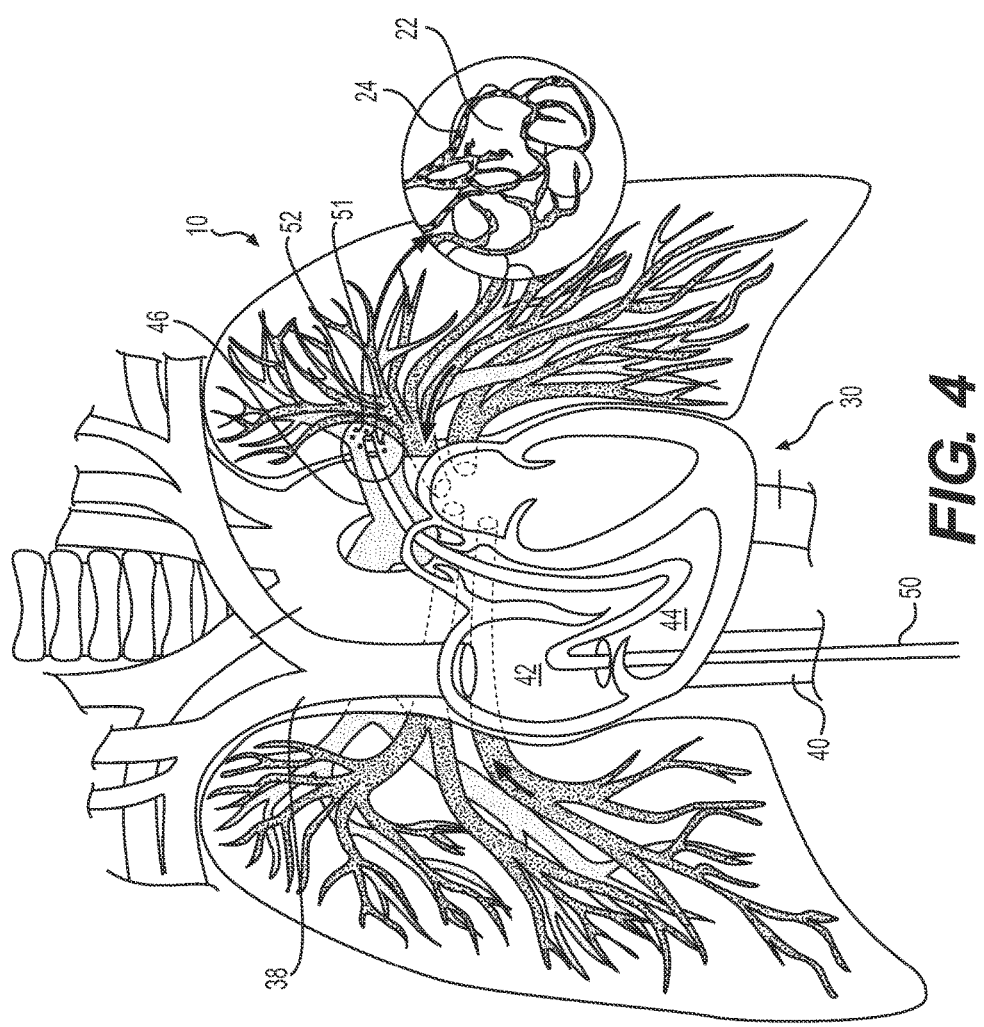
FIG. 4 illustrates an exemplary embodiment of a device deploying an exemplary media in a blood vessel of FIG. 3.
Figure 5A:
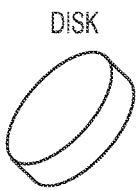
FIGS. 5A-5F illustrate exemplary embodiments of media that may be deployed in the blood vessel of FIG. 3.
Figure 5B:
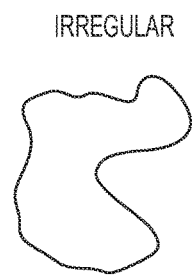
Figure 5C:
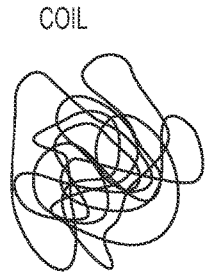
Figure 5D:
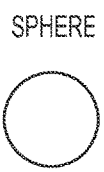
Figure 5E:
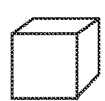
Figure 5F:
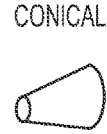

In some embodiments of the invention, a media 52 may be released into the blood stream flowing from the heart to the lungs 10 to treat the lungs 10. In some embodiments, the media 52 may block the flow of blood through the blood vessel downstream from the release site. FIG. 4 illustrates one embodiment of an invention in which a steerable catheter 50 is inserted through the pulmonary artery 46 to a selected arteriole 48 to release the media 52. The media 52 may block the blood flow to the capillaries 24 surrounding a targeted group of alveoli 22. When blood flow to a region of lung 10 is blocked, cell death occurs due to a lack of oxygen. The dead tissue shrivels up and becomes less elastic, effectively resulting in lung volume reduction. As explained previously, elimination of the diseased portion of a lung 10 improves overall lung function.

Any luminar device, such as catheter 50, may be used to deploy the media 52 into the blood vessel. The catheter 50 may extend from a proximal end positioned external to the body to a distal end that is (endoscopically, percutaneously, laproscopically, or surgically) inserted into the body and steered to a desired location of the pulmonary artery 46. In some embodiments, the catheter 50 may include one or more radiopaque or other markers (not shown) to assist in suitably positioning the catheter 50 in the blood vessel. The catheter 50 may be configured to direct the media 52 into the blood stream through its distal end. The proximal end of the catheter 50 may include one or more steering dials (or other mechanisms) configured to articulate (or turn) its distal end in different directions. The distal end of the catheter 50 may include one or more orifices 51 adapted to discharge the media 52 into the blood vessel. In general, the orifice(s) 51 may be of any size and shape, and arranged in any pattern. In some embodiments, as illustrated in FIG. 4, the distal-most tip of the catheter 50 may be open to form a single orifice 51. Although the catheter 50 is described as being directly introduced into the blood vessel, in some embodiments, the catheter 50 may be introduced into the blood vessel via another luminal delivery device, such as a guide tube, etc. In some embodiments, the catheter 50 may also include a retention member (such as, a balloon (not shown)) to maintain the position of catheter 50 within a blood vessel. In some embodiments, the catheter 50 may include an injector or a reservoir (not shown) at the proximal end to store the media 52. It is contemplated that the injector may include a heater to maintain the media 52 at a desired temperature. Depressing a plunger of the injector directs the media 52 towards the distal end of the catheter 50.

In use, a user (such as, a physician, etc.) may insert the distal end of the catheter 50 into the body, and advance the catheter 50 into the heart 30 through the superior or inferior vena cava 38, 40. The user may then guide the catheter 50 into the pulmonary artery 46 through the right ventricle 44. The catheter 50 may then be steered to a targeted area of the lung 10 (such as, for example, an arteriole 48 leading to a targeted alveoli 22). After the catheter 50 is suitably positioned in the pulmonary artery 46, the media 52 may be released into the blood stream. The media 52 may block the flow of blood through a blood vessel (for example, through an arteriole 48 leading to a targeted alveoli 22). The catheter 50 may now be moved to another location to discharge the media 52 at the new location. After all the desired locations have been treated, the catheter 50 may be withdrawn from the body. In some embodiments, similar to a procedure commonly used by interventional physicians, a contrast material may first be injected at the site and a fluoroscopic image obtained to confirm the location of a media discharge site within the pulmonary circulation before discharging the media 52. It is also contemplated that embedded fluoroscopic tags may be discharged at a site along with the media 52. These tags may assist a physician in identifying locations where the media 52 were previously deployed. In some embodiments, these tags may include radiopaque filler materials mixed with a polymer material, or a radiopaque metal component within the polymer, or simply a radiopaque metal material.

To assist in steering the catheter 50 to the desired location in the pulmonary artery 46, in some embodiments, one or more light sources (fiber optic cables, light-emitting diodes, etc.) and/or image sensors may be provided on the catheter 50. Additionally or alternatively, in some embodiments, the catheter 50 may include one or more radiopaque markers (not shown), and the user may direct the catheter 50 under x-ray fluoroscopy or radiography to the proper location in the pulmonary artery 46. The catheter 50 may be introduced into the pulmonary artery 46 directly, or may be introduced through a lumen of another device (such as, for example, an overtube, guide tube, etc.). While a catheter 50 is referred to and described herein, it is to be understood that any luminal delivery device may be used without departing from the scope of the disclosure.

Although the catheter 50 is described as being introduced into the pulmonary artery 46 through the superior or inferior vena cava 38, 40, this is only exemplary. The catheter 50 may be introduced into the pulmonary artery 46 by any known procedure. Since such procedures are well known in the field of interventional cardiology, these techniques will not be discussed herein. Further, although the catheter 50 is described as being inserted into the pulmonary artery 46, in general, the catheter 50 may be inserted into any blood vessel directing blood to the lungs 20. For instance, although only about 10% of the blood supply to the lungs 10 is directed through the bronchial artery (not shown), it is contemplated that in some embodiments the catheter 50 may be additionally or alternatively inserted into the bronchial artery to deploy the media 52 therein.

In some embodiments, a temporary media may first be deployed through the catheter 50 to enable the user to correctly position the catheter for subsequent deployment of a blood-blocking media 52. The temporary media may block the blood supply to a region of the lungs 10 for a relatively short time (e.g. 1 to 5 minutes) before dissolving and restoring blood supply to the affected region. This temporary blood flow blockage may enable the user to perform diagnostic checks to determine if the desired region of the lung 10 has experienced blockage. If it is determined that the temporary media reached the desired region of the lung, the blood-blocking media 52 may now be deployed. In such embodiments, the catheter 50 may remain in the same position for both the temporary and blood-blocking media 52 deployment. If the user desires to reposition the catheter 50 to target a different region of the lung, the user may reposition the catheter 50 and repeat the temporary media deployment until the proper catheter location is identified. In some embodiments, in place of a dissolvable temporary media, a dye which can be imaged from outside the body may be used to determine the proper positioning of the catheter prior to deployment of the media 52. In some embodiments, the blood-blocking media 52 may be configured to degrade, dissolve, or otherwise dissipate in the presence of a chemical or a type of radiant energy. In such embodiments, if after blocking blood flow in a blood vessel using the media 52, the media 52 is determined to be unsuitable for the patient, the media 52 may be exposed to a chemical or a type of radiant energy (light, radiation, sound waves, etc.) to degrade the media 52 and allow blood flow to restart through the blood vessel. The energy source may be delivered to the blood vessel through a catheter or may be located outside the body of the patient.

In general, any type of substance that will eventually block the flow of blood through the blood vessel may be used as the media 52. The media 52 may have any shape (regular shape or irregular shape) and configuration. FIGS. 5A-5F illustrate some exemplary shapes of media 52 that may be deployed into the blood vessel. In some embodiments, the media 52 may be substantially disk shaped, substantially cube shaped, substantially conical, etc. A conical configuration of the media 52 may assist in wedging of multiple pieces of the media 52 in a blood vessel. In some embodiments, the media may have an irregular coil like configuration. A coil shaped media 52 may conform to various geometries seen in a blood vessel, and may therefore, assist in efficiently blocking the blood vessel. In some embodiments, the media 52 may be spherical for ease of delivery through the catheter. In some applications, a spherical media 52 may be the preferred shape for discharge in generally circular cross-sectioned blood vessels. In some embodiments, the media 52 may have regular or irregular nesting shapes. In such embodiments, after deployment, a plurality of media 52 may interlock to collectively occlude or block the blood vessel. In some embodiments, the media 52 may be drug-eluting. That is, the media 52 may include a drug or a chemical that promotes necrosis of the lung tissue. The drugs could be embedded in the media 52, coated on the surface of the media 52, or may be compounded with the media 52 in the form of microspheres or particulates. In some embodiments, where a drug is coated on the surface of the media, the media may be porous so that the coating sticks to the media well and elutes over a longer period of time.

Figure 6:
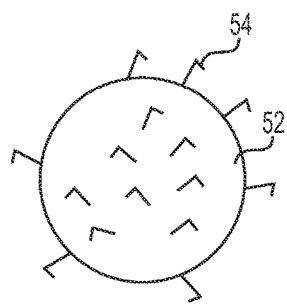
FIG. 6 is a diagrammatic illustration of an exemplary media that may be deployed in the blood vessel of FIG. 3.

In some embodiments, the media 52 may be configured to expand (such as, for example, radially outward) or swell when deployed into the blood vessel (for example, when the media 52 comes into contact with humidity, after exposure to blood for a certain time, etc.). In such embodiments, a relatively small-sized media 52 discharged at a site may travel downstream with the blood and gradually expand in size to block the blood vessel downstream of the discharge site. In some embodiments, the media 52 may include expandable microspheres comprising a thermoplastic shell encapsulating a low boiling point liquid hydrocarbon. When the temperature of the microsphere reaches a threshold value, the thermoplastic shell softens. The increasing pressure of the hydrocarbon within the microsphere will then cause the microsphere to expand in volume. In some embodiments, the microsphere dissolves to expose a constrained (unexpanded) state of another material. This material may then expand to fill the blood vessel. In some embodiments, as illustrated in FIG. 6, the media 52 (expandable or non-expandable media 52) may include surface modifications (such as, for example, Velcro® loops, barbs 54, or other locking features) that assist in interlocking the media together. Alternatively or additionally, these surface modifications may serve to anchor the media 52 on tissue. It is contemplated that, in some embodiments, the barbs 54 form on the surface of the media 52 only after the media 52 is deployed in a blood vessel. For instance, after exposure to humidity for a certain time, the barbs 54 extend (or disentangle) from the surface of the media 52.

In some embodiments, the media 52 may be a solid (metal, polymer, a composite of multiple materials, etc.). In some embodiments, a fluid of a gel type substance may be used as media 52. After its release, this substance may gradually solidify as its travels downstream with the blood. For instance, in some embodiments, a drug suspension mixed with a biodegradable polymer having a low glass transition temperature (Tg), may be used as the media 52. In such embodiments, the media 52 may be heated above its Tg and discharged into the blood stream. As the media 52 cools below its Tg, it solidifies to occlude the blood vessel. It is also contemplated that in some embodiments, a liquid type media 52 (for example, a chemical) may be discharged from the catheter 50 to necrose a selected region of blood vessel or lung tissue.

Media 52 may be discharged into the blood vessel continuously or in batches. That is, in some embodiments, the catheter 50 may deliver a first batch of media 52 at a first time and a second batch at a second time after the first time. Each batch may include any amount (number, volume, etc.) of media 52. In some embodiments, a pressurized fluid may assist in pushing the media 52 out of the catheter 50. In such embodiments, the media 52 may be released into the blood vessel along with the pressurized fluid. In such embodiments, the catheter 50 may be coupled to a pressurized fluid source (not shown). In some embodiments, the media 52 may be bioabsorbable over a period of time (for example, a few days, weeks months, etc.) sufficient to necrose the desired tissue due to lack of blood flow.

Although the exemplary embodiments described above have been disclosed in connection with devices for treating blood vessels, those skilled in the art will understand that the principles set out above can be applied to any device and can be implemented in different ways without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Moreover, while specific exemplary embodiments may have been illustrated and described herein, it should be appreciated that combinations of the above embodiments are within the scope of the disclosure. Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

What is claimed is:

1. A method of treating a lung, comprising:
deploying a catheter into a blood vessel directing blood towards a portion of the lung; and
discharging a first media into the blood vessel through the catheter, the first media being configured to at least partially block a flow of blood within the portion of the lung, wherein the first media degrades and permits restoration of the flow of blood within the portion of the lung after a first time period;
evaluating the flow of blood in the blood vessel after discharging the first media and before the first media degrades; and
based on the evaluation, discharging a second media into the blood vessel to block the flow of blood within the portion after degradation of the first media, wherein the second media is different from the first media.

2. The method of claim 1, wherein deploying the catheter into a blood vessel includes deploying the catheter into a pulmonary artery.

3. The method of claim 1, wherein the second media is one of a solid or a gel that solidifies in the blood vessel.

4. The method of claim 1, wherein after discharge in the blood vessel and after a determination that the second media is unsuitable for the lung, removing the second media from the lung by application of a chemical or a radiant energy.

5. The method of claim 1, wherein deploying the catheter includes deploying the catheter into a blood vessel that directs blood from a heart to the lung.

6. The method of claim 1, wherein discharging a second media includes discharging a second media including an expandable microsphere having a thermoplastic shell encapsulating a liquid hydrocarbon, and after discharge of the second media into the blood vessel, the thermoplastic shell softens and expands.

7. The method of claim 1, wherein discharging a second media includes discharging a plurality of second media that interlock to at least partially block the flow of blood within the portion.

8. The method of claim 1, wherein the second media elutes a drug that causes necrosis of tissue.

* * * * *